United States Patent
Biedermann et al.

(10) Patent No.: US 8,206,424 B2
(45) Date of Patent: Jun. 26, 2012

(54) BONE ANCHORING NAIL

(75) Inventors: Lutz Biedermann, VS-Villingen (DE); Wilfried Matthis, Weisweil (DE)

(73) Assignee: Biedermann Technologies GmbH & Co. KG, Donaueschingen (DE)

( * ) Notice: Subject to any disclaimer, the term of this patent is extended or adjusted under 35 U.S.C. 154(b) by 0 days.

(21) Appl. No.: 12/844,588

(22) Filed: Jul. 27, 2010

(65) Prior Publication Data

US 2010/0292741 A1     Nov. 18, 2010

Related U.S. Application Data

(63) Continuation of application No. 11/870,326, filed on Oct. 10, 2007, now Pat. No. 7,785,356.

(60) Provisional application No. 60/858,175, filed on Nov. 10, 2006.

(30) Foreign Application Priority Data

Nov. 10, 2006    (EP) ..................................... 06023443

(51) Int. Cl.
     *A61B 17/04*      (2006.01)
     *A61B 17/84*      (2006.01)

(52) U.S. Cl. ......... 606/304; 606/300; 606/305; 606/314

(58) Field of Classification Search .................... 606/76, 606/92, 93, 246, 300–321; 604/890.1, 285, 604/264; 411/464
See application file for complete search history.

(56) References Cited

U.S. PATENT DOCUMENTS

| 5,743,912 | A | * | 4/1998 | Lahille et al. .................. 606/65 |
| 6,214,012 | B1 | | 4/2001 | Karpman et al. |
| 7,785,356 | B2 | * | 8/2010 | Biedermann et al. ......... 606/309 |
| 2004/0147929 | A1 | | 7/2004 | Biedermann et al. |
| 2004/0220575 | A1 | | 11/2004 | Biedermann et al. |
| 2005/0059972 | A1 | | 3/2005 | Biscup |
| 2006/0089642 | A1 | | 4/2006 | Diaz et al. |

FOREIGN PATENT DOCUMENTS

| EP | 0784967 A2 | 7/1997 |
| EP | 1430846 A1 | 6/2004 |
| JP | 9149906 | 6/1997 |
| WO | WO 01/26568 A1 | 4/2001 |
| WO | WO 2006/070961 A2 | 7/2006 |

OTHER PUBLICATIONS

European Search Report, dated May 10, 2007, corresponding to EP 06023443; European Search Report mailed May 22, 2007; Biedermann Motech GmbH (4 pp.).

\* cited by examiner

*Primary Examiner* — Eduardo C Robert
*Assistant Examiner* — Christina Negrelli
(74) *Attorney, Agent, or Firm* — Christie, Parker & Hale, LLP

(57) ABSTRACT

A bone anchoring nail is provided having a threadless shaft with a free end, a head opposite to the free end, the head having a substantially U-shaped recess for accommodation of a rod or a rod-shaped element, a longitudinal bore extending through the shaft and opening towards any one of the head and the free end and a plurality of openings extending through the wall of the shaft and being in communication with the bore. The bone anchoring nail allows quick insertion and reliable fixation enhanced by the in-growth of blood vessels.

13 Claims, 4 Drawing Sheets

BONE ANCHORING NAIL

CROSS-REFERENCE TO RELATED APPLICATION(S)

This application is a continuation of allowed application Ser. No. 11/870,326 filed Oct. 10, 2007 now U.S. Pat. No. 7,785,356 which claims the benefit of U.S. Provisional Patent Applicant Ser. No. 60/858,175, filed Nov. 10, 2006, and claims priority from European Patent Application EP 06023443.2, filed Nov. 10, 2006, the disclosures of which are incorporated herein by reference.

BACKGROUND

The present invention relates to a bone anchoring nail. In particular, it relates to a bone anchoring nail having a shaft with a longitudinal bore and a plurality of openings in the wall of the shaft, and a head with a substantially U-shaped recess for accommodation of a rod. The bone anchoring nail can be used, for example, for anchoring a spinal rod in the pedicles of adjacent vertebrae for stabilizing the spinal column or it can be used in any other type of bone anchor application using a rod or a rod-shaped element.

A bone anchoring device in form of a bone screw comprising a screw head and a threaded shaft, wherein an axial bore is provided which is connected to the outside through a plurality of radial bores is known from WO 01/26568. Bone cement can be injected through the bone screw and into the bony tissue surrounding the threaded shaft. US 2004/0147929 A1 discloses a bone anchoring device having a tubular element having a section with a bone thread on its outer wall, a tip and a head which can be connected to the tubular element, wherein the head comprises a U-shaped recess for receiving a rod. The insertion of such a bone anchoring device is accomplished by screwing-in which is force and time consuming. Further, during screwing, forces act onto the bone which can be too large in certain situations, for example in the case of older and/or weak bones.

US 2004/0220575 A1 discloses a bone anchoring element for anchoring an external device in the bone. The bone anchoring element comprises a head which is connectable to the external device and a shaft connected to the head, wherein the shaft has a predetermined section with a bone thread and at least one bone thread-free section within said predetermined section. The bone anchoring device can be pushed into a predrilled hole in the bone and then turned so as to allow anchoring by means of the bone thread. The anchoring device can be unscrewed due to the presence of the bone thread. In a specific embodiment the shaft comprises a longitudinal bore with radial bores leading to the outside for the purpose of allowing the introduction of a medical agent or bone cement into the pre-drilled hole.

U.S. Pat. No. 5,743,912 and JP 09149906 A disclose medical implants comprising a shaft with a longitudinal bore and radial openings and a threaded section at one end.

US 2006/0089642 A1 describes an implant for vertebrae and other bones which is formed as an elongated cylindrical body with a series of perforations penetrating the cylinder wall and communicating with the cylinder bore. The bore may be filled with a bone growth mixture. The implant is not suitable for connection with a spinal stabilization rod.

For certain clinical requirements, in particular for the stabilization of weak osteoporotic bone, in pediatric surgery, in surgery of the cervical spine or in neurosurgery, there is a need for bone anchoring devices which can be connected to an external stabilization rod or rod-shaped element, wherein the bone anchoring devices can be inserted even more quickly and with lower insertion forces than the known devices while providing a safe fixation which is comparable to that of screws.

SUMMARY

The bone anchoring nail according to the invention allows a fast insertion into a core hole which is provided in the bone in advance. A reliable and lasting fixation is accomplished by in-growth of vessels into the openings followed by newly formed bone into the openings and/or by the injection of bone cement through the longitudinal bore which exits through the openings, hardens and connects the nail to the surrounding bone material.

The bone anchoring nail is specifically applicable to minimally invasive surgery (MIS), to spinal surgery and to the stabilization of long bones.

Further features and advantages of the invention will become apparent and will be best understood by reference to the following detailed description of embodiments taken in conjunction with the accompanying drawings.

DETAILED DESCRIPTION

Figure 1:
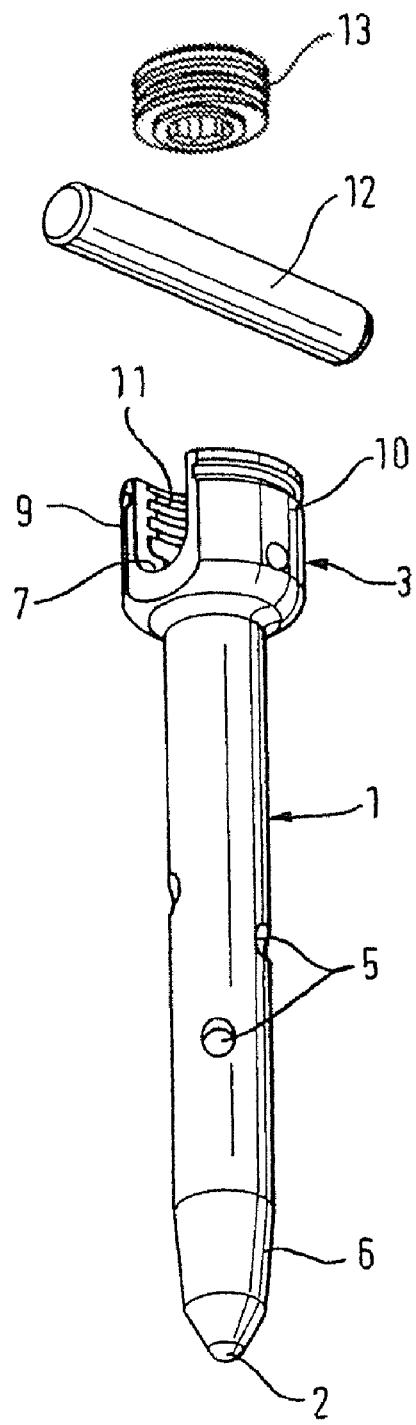
FIG. 1 shows a perspective exploded view of a bone anchoring nail according to a first embodiment.
Figure 2:
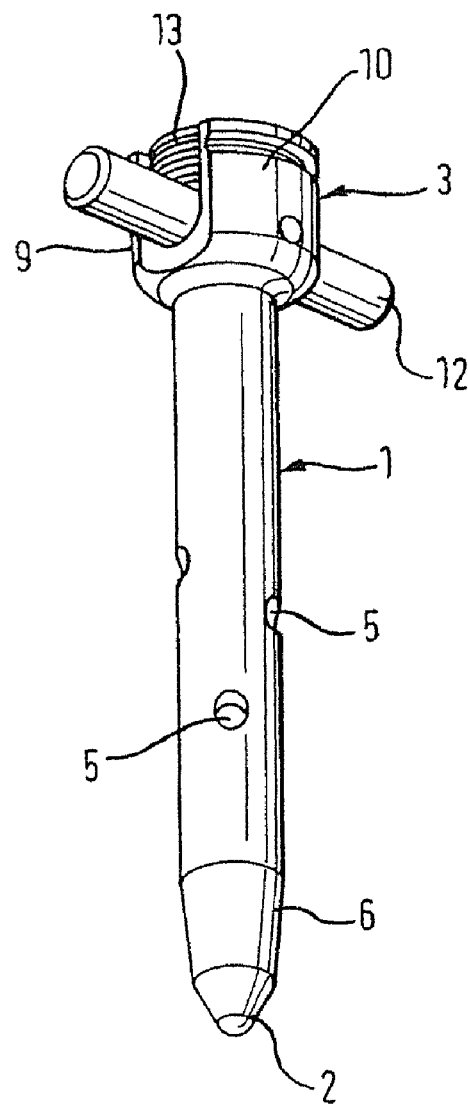
FIG. 2 shows the bone anchoring nail according to FIG. 1 in an assembled state connected to a rod.
Figure 3:
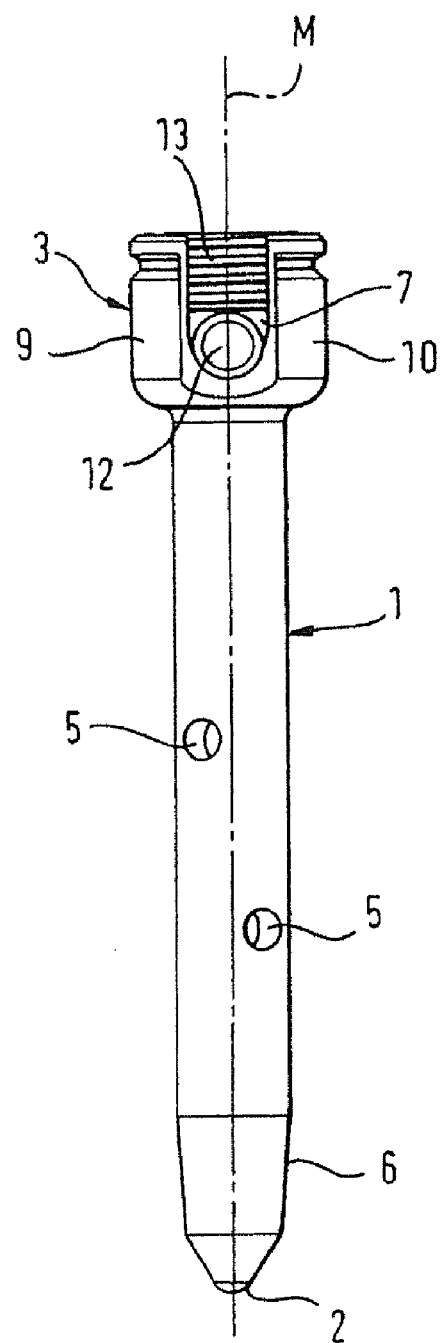
FIG. 3 shows a side view of the bone anchoring nail with the rod according to the first embodiment in a direction along the rod axis.
Figure 4:
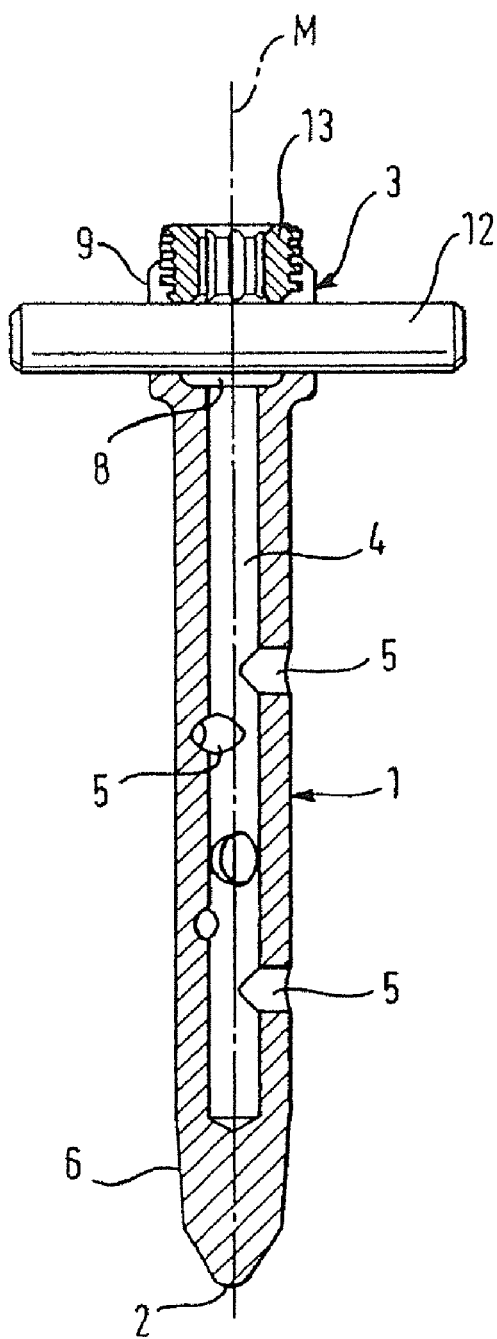
FIG. 4 shows a sectional view of the bone anchoring nail with the rod according to the first embodiment, the section being taken along the rod axis.

A bone anchoring nail according to a first embodiment of the invention is described with reference to FIGS. 1 to 4. The bone anchoring nail comprises a shaft 1 having a free end 2 and head 3 opposite to the free end 2. A coaxial bore 4 extends through the shaft from the end where the head 3 is located up to a distance from the free end 2. The diameter of the coaxial bore 4 is such that the shaft has sufficient strength against failure.

A plurality of openings 5 extend in a radial direction from the bore 4 through the wall of the shaft 1 to the outside. The cross-section of the openings is preferably circular or otherwise rounded. The openings can be arranged in a regular manner, such as, for example, in circumferential rows wherein one row is offset with regard to another row such as to provide a uniform distribution of openings in a section of the shaft 1. As shown in the drawings, there can be a section of the shaft 1 which is adjacent to the head 3 where no openings are provided. The number and arrangement of the openings is varied according to the clinical requirements. The diameter of the openings is at least as large so that blood vessels from the surrounding bone material can grow-in followed by the formation of new bone into the openings. Also, the diameter of the opening is selected such that bone cement and/or medical treatment agents can exit through the openings without clogging. At the outer wall of the shaft 1 a countersink area (not shown) around the openings can be provided to facilitate in-growth. The openings 5 are shown to extend in a radial direction with respect to the shaft axis M. However, some or all of them may also extend in a direction including an angle with the axial bore which is different from 90°. The length of the shaft is selected so as to be suitable for the specific application.

The free end 2 is shaped as a tip. However, free end 2 also can be flat. The shaft 1 can taper to the free end 2 in a section 6, for example, it can taper in a conical shape. The coaxial bore 4 can also extend over the full length of the shaft 1 up to the free end 2 such that it provides an opening at the free end 2. Also, the tip can be provided as a separate part connectable to the shaft 1. In this case, the coaxial bore 4 may be closed by connecting a separate tip to the shaft. As shown in the drawings, the outer surface of the shaft 1 is threadless. In addition, the outer surface of the shaft 1 can be treated to provide an enhanced fixation or to enhance slidability of the shaft in the core hole. For example, the outer surface can be roughened to enhance fixation or coated with a material promoting in-growth. In another example, the surface can be coated or polished or otherwise treated to enhance slidability to facilitate insertion.

The head 3 is, in the embodiment shown, substantially cylindrically-shaped with an outer diameter which is larger than the diameter of the shaft 1. The head 3 comprises a substantially U-shaped recess 7 and a coaxial bore 8 which extends through the head and is in communication with the coaxial bore 4 of the shaft. By means of the U-shaped recess 7 two free legs 9, 10 are formed which are provided with an internal thread 11. The diameter of the U-shaped recess 7 is such that a rod 12, used for connecting several of the bone anchoring nails with each other, can be inserted. The rod 12 is secured by a locking element, for example by an inner screw 13 which can be screwed-in between the legs 9, 10 and which presses onto the rod.

In the embodiment shown the head 3 and the shaft 1 are designed as a single part. However, the head 3 and the shaft 1 can also be designed as separate parts, wherein the head 3 and the shaft 1 can be rigidly connected with each other so as to form a rigid monoaxial connection. Alternatively, the head 3 and the shaft 1 can be rotatably connected, the rotation axis being the shaft axis.

The locking element can be realized otherwise than by an inner screw 13. For example, a combination of an outer nut which cooperates with an outer thread on the head 3 and an inner screw can be provided. Alternatively, another locking mechanism is conceivable, for example, a bayonet coupling between the locking element and the head.

The bone anchoring nail is made of a biocompatible material, such as titanium or a titanium alloy or a biocompatible plastic material. It can also be made from a shape memory alloy.

In operation, first, a core hole is prepared in the bone area where the bone anchoring nail is to be anchored. The inner diameter of the hole corresponds to the outer diameter of the shaft or is slightly smaller. The shaft 1 is then pushed or pressed into the core hole. If the shaft 1 is pressed into the core hole it holds due to the frictional forces. The action of inserting the shaft into the hole is considerably less time consuming than screwing a bone screw into the bone, even if a pre-drilled hole is used for the bone screw. Hence, the bone anchoring nail can be used in such clinical situations, in which a very quick insertion is necessary and/or in which weakness of the bone material does not allow the application of large insertion forces which may occur in the case of using a bone screw.

After inserting at least two bone anchoring nails they can be connected via the rod. The rod is fixed by tightening the inner screw. The bone anchoring nail can also be combined with conventional monoaxial bone screws which are used for connection with rods.

After some time blood vessels may begin to grow-in through the openings 5 into the coaxial bore 4 followed by the formation of new bone, thereby enhancing the fixation. For further enhancing the fixation a bone cement such as for example Polymethylmethacrylate (PMMA) or Tricalcium Phosphates (TCP) can be introduced through the bore 8 of the head and the longitudinal bore 4 of the shaft before inserting the rod. The bone cement is in a substantially fluid form and exits through the openings 5. When it hardens, it firmly connects the shaft 1 with the surrounding bone material.

Figure 5:
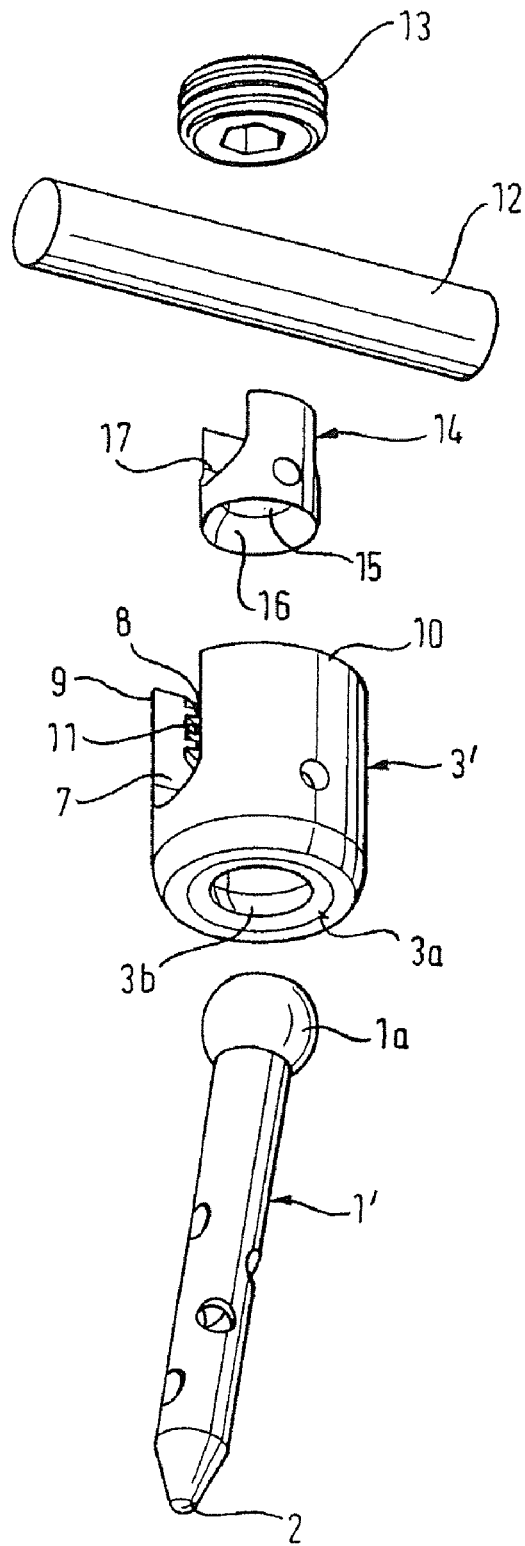
FIG. 5 shows an exploded perspective view of the bone anchoring nail according to a second embodiment.
Figure 6:
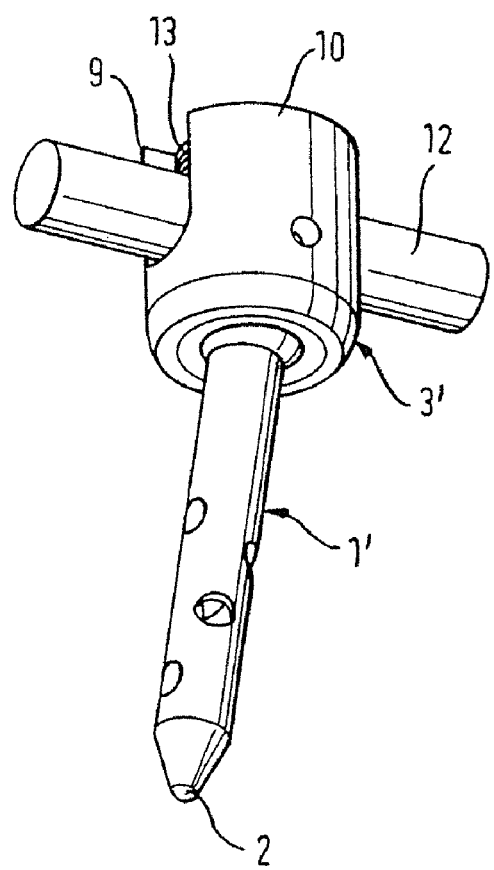
FIG. 6 shows the bone anchoring nail according to the second embodiment in an assembled state connected to a rod.
Figure 7:
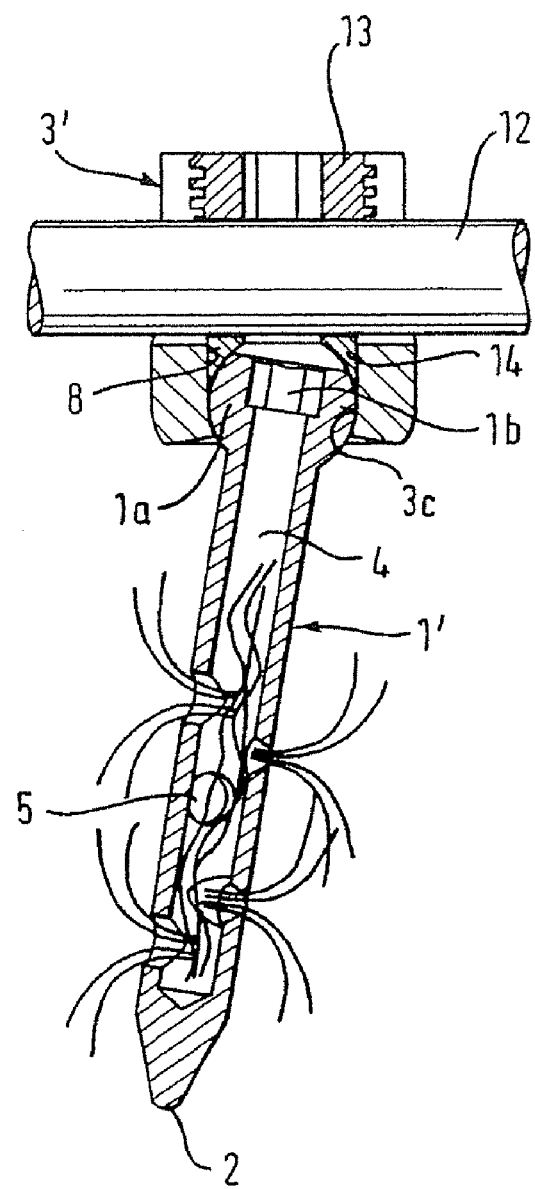
FIG. 7 shows a sectional view of the bone anchoring nail of the second embodiment connected to a rod, the section be taken along the rod axis and a schematic view of the in-growth of vessels.

A second embodiment is shown in FIGS. 5 to 7. The second embodiment differs from the first embodiment in that the head and the shaft are configured as separate parts which are pivotably connected so as to allow a polyaxial adjustment. Parts which are identical to the first embodiment are designated with the same reference numerals. The shaft 1' differs from the first embodiment in that it has a spherical segment-shaped end section 1a through which the longitudinal bore 4 extends. On its free end the spherical segment-shaped end section 1a comprises a recess 1b for engagement with a screwing-in tool.

The head 3' is formed as a separate part. It has, like the head 3 of the first embodiment, a substantially cylindrical shape with a substantially U-shaped recess 7 and a coaxial bore 8 by means of which two legs 9, 10 are formed on which an internal thread 11 is provided. The head 3' has a lower side 3a with an opening 3b which is dimensioned such that spherical segment-shaped head 1a cannot fall out in the assembled state. Between the bore 8 and the opening 3b a seat 3c for the spherical segment-shaped end section 1a is provided. In the assembled state, the shaft 1' can pivot relative to the head 3'.

The bone anchoring nail according to the second embodiment further comprises a pressure element 14 which is substantially cylindrically-shaped with a coaxial bore 15 and a spherical section 16 suitable to press on to the end section 1a. In the embodiment shown the pressure element 14 has a substantially U-shaped recess 17 opposite to the spherical section 16 for receiving the rod 12. The pressure element 14 can be secured within the head 3' against rotation and against falling out. Preferably, the shaft 1', the head 3' and the pressure element 14 are preassembled.

Use of the bone anchoring nail according to the second embodiment is similar to that of the first embodiment. The bone anchoring nail according to the second embodiment allows a polyaxial adjustment of the head 3' with respect to the shaft 1'. The angular position of the shaft 1' relative to the head 3' is locked by pressing the pressure element 14 onto the spherical segment-shaped end section 1a which presses the spherical segment-shaped end section 1a against the seat 3c. Locking is accomplished by tightening the inner screw such that the rod 12 is fixed and transmits the force onto the pressure element 14 which then blocks the spherical segment-shaped end section 1a.

In a modification, the spherical segment-section 1a of the shaft 1' and the rod 12 can be locked independently from each other.

FIG. 7 schematically shows the in-growth of blood vessels through the openings 5. The vessels extend through the openings and can further continue to grow in the coaxial bore 4.

Figure 8:
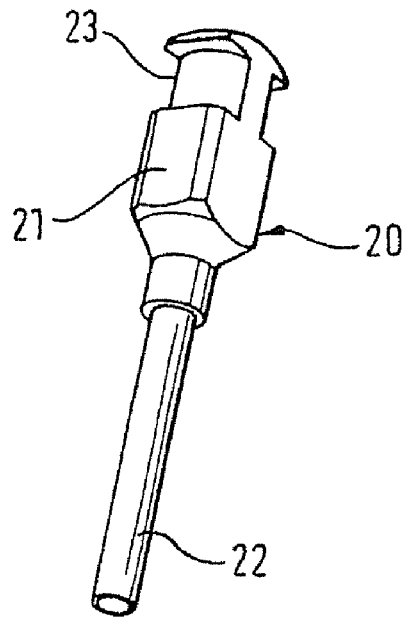
FIG. 8 shows an injection device for injecting medical treatment agents or bone cement.

FIG. 8 schematically shows an injection instrument 20 for injecting bone cement or a medical treatment agent into the shaft 1, 1'. The injection instrument 20 comprises a reservoir 21 for the agent or the bone cement, an injection tube 22 and an actuator 23 for actuating the injection. The injection tube 22 has an outer diameter which is smaller than the diameter of the coaxial bore 4 such that it can be introduced to such an extent into the coaxial bore 4 that it reaches the vicinity of the openings.

While a particular form of the disclosure has been illustrated and described, it will be apparent that various modifications can be made without departing from the spirit and scope of the disclosure. Accordingly, it is not intended that the disclosure be limited, except as by the appended claims.

What is claimed is:

1. A bone anchoring nail comprising:
   a shaft with a free end,
   a head opposite to the free end along a longitudinal axis of the shaft, the head having a substantially U-shaped recess forming two legs for accommodation of a rod-shaped element between the two legs,
   a locking element configured to secure to the head to lock a rod-shaped element in the U-shaped recess,
   a longitudinal bore extending into the shaft and opening towards at least one of the head and the free end,
   the shaft comprising a shaft section having a first end and a second end that are spaced apart along the longitudinal axis,
   wherein the shaft section comprises a plurality of openings extending through a wall of the shaft and being in communication with the bore, and
   wherein at least the shaft section is threadless along its entire exterior surface.

2. The bone anchoring nail of claim 1, wherein the bore is open towards the head and closed at the second end.

3. The bone anchoring nail of claim 1, wherein the shaft has a substantially cylindrical shape.

4. The bone anchoring nail of claim 1, wherein the openings have a round cross-section.

5. The bone anchoring nail of claim 1, wherein the openings extend in a radial direction from the shaft axis.

6. The bone anchoring nail of claim 1, wherein the exterior surface of the shaft section is roughened to enhance fixation.

7. The bone anchoring nail of claim 1, wherein the shaft and the head are mono-axially connected.

8. The bone anchoring nail of claim 1, wherein all openings extending through the wall of the shaft and in communication with the bore are located in the shaft section.

9. The bone anchoring nail of claim 1, wherein the first end of the shaft section is closer to the head than the second end of the shaft section and the entire exterior surface of the shaft is threadless from the free end to the first end of the shaft section.

10. A method of anchoring a bone anchoring nail to a bone, the bone anchoring nail comprising:
    a shaft with a free end,
    a head opposite to the free end along a longitudinal axis of the shaft, the head having a substantially U-shaped recess forming two legs for accommodation of a rod-shaped element between the two legs,
    a longitudinal bore extending into the shaft and opening towards at least one of the head and the free end,
    the shaft comprising a shaft section having a first end and a second end that are spaced apart along the longitudinal axis,
    wherein the shaft section comprises a plurality of openings extending through a wall of the shaft and being in communication with the bore,
    wherein at least the shaft section is threadless along its entire exterior surface,
    the method comprising:
    creating a core hole in a bone;
    inserting the shaft into the core hole; and
    inserting a rod-shaped element in the U-shaped recess and securing the rod shaped element in the U-shaped recess.

11. The method of claim 10, further comprising inserting bone material in the longitudinal bore.

12. A bone anchoring nail assembly comprising:
    a bone anchoring nail, comprising:
      a shaft with a free end,
      a head opposite to the free end along a longitudinal axis of the shaft, the head having a substantially U-shaped recess forming two legs for accommodation of a rod-shaped element between the two legs,
      a longitudinal bore extending into the shaft and opening towards at least one of the head and the free end,
      the shaft comprising a shaft section having a first end and a second end that are spaced apart along the longitudinal axis,
      wherein the shaft section comprises a plurality of openings extending through a wall of the shaft and being in communication with the bore, and
      wherein at least the shaft section is threadless along its entire exterior surface; and
    a rod-shaped element configured to be received in the U-shaped recess of the head such that it can be fastened in the U-shaped recess of the head.

13. The bone anchoring nail assembly of claim 12 wherein the shaft and the head are monolithic.

* * * * *